United States Patent [19]

Kornfeld et al.

[11] 4,198,415

[45] Apr. 15, 1980

[54] PROLACTIN INHIBITING OCTAHYDRO PYRAZOLO[3,4-g]QUINOLINES

[75] Inventors: Edmund C. Kornfeld; Nicholas J. Bach, both of Indianapolis, Ind.

[73] Assignee: Eli Lilly and Company, Indianapolis, Ind.

[21] Appl. No.: 31,641

[22] Filed: Apr. 19, 1979

Related U.S. Application Data

[63] Continuation-in-part of Ser. No. 5,061, Jan. 22, 1979, abandoned.

[51] Int. Cl.² .................. A61K 31/47; C07D 471/04
[52] U.S. Cl. .................................... 424/258; 546/82; 546/158; 546/164; 546/165; 546/166
[58] Field of Search ................ 546/82; 424/258

[56] References Cited

U.S. PATENT DOCUMENTS

| | | |
|---|---|---|
| 3,084,165 | 4/1963 | Schellhammer et al. ......... 546/82 X |
| 3,600,393 | 8/1971 | Graeve et al. ................. 546/82 |
| 3,859,291 | 1/1975 | Burch ........................ 546/82 |

*Primary Examiner*—John D. Randolph
*Assistant Examiner*—Richard A. Schwartz
*Attorney, Agent, or Firm*—James L. Rowe; Arthur R. Whale

[57] ABSTRACT

Octahydropyrazolo[3,4-g]quinolines, dopamine agonists, useful in treatment of Parkinsonism and in inhibiting secretion of prolactin.

16 Claims, No Drawings

PROLACTIN INHIBITING OCTAHYDRO PYRAZOLO[3,4-g]QUINOLINES

This application is a continuation-in-part of application Ser. No. 5,061, filed Jan. 22, 1979, now abandoned.

DESCRIPTION OF THE INVENTION

This invention provides octahydropyrazolo[3,4-g]quinolines of the formula:

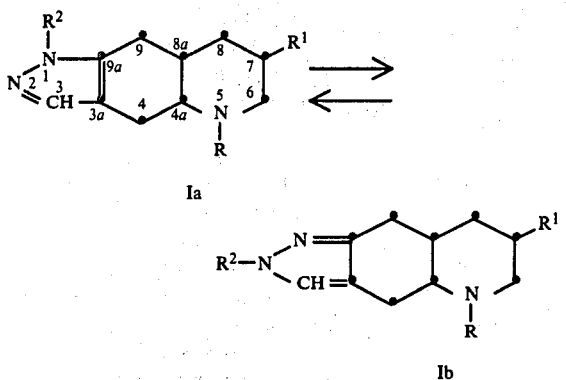

wherein R is H, Cn, (C$_1$-C$_3$) alkyl, allyl or benzyl; R$^1$ is H, COOZ' or CH$_2$X wherein Z' is H, (C$_1$-C$_2$)-alkyl or phenyl-substituted (C$_1$-C$_2$)alkyl and X is Cl, I, Br, OH, OCH$_3$, SCH$_3$, CN, OSO$_2$(C$_1$-C$_3$)alkyl, OSO$_2$phenyl, OSO$_2$tolyl, SO$_2$CH$_3$ or CO—NH$_2$; and R$^2$ is SO$_2$-C$_1$-C$_3$)alkyl, SO$_2$phenyl, SO$_2$tolyl, or H; and pharmaceutically-acceptable acid addition salts thereof. Compounds according to the above formulas in which R is C$_1$-C$_3$ alkyl or allyl and R$^1$ is H or CH$_2$X where X is CN, SCH$_3$, SO$_2$CH$_3$, OCH$_3$ or CONH$_2$ and their pharmaceutically acceptable acid addition salts are useful chiefly as dopamine agonists, while these compounds in which R is H, CN, C$_1$-C$_3$ alkyl, allyl or benzyl and R$^1$ is COOZ' or CH$_2$X wherein Z' is H, (C$_1$-C$_2$)alkyl or phenyl-substituted (C$_1$-C$_2$)-alkyl and X is Cl, Br, I, OH, OSO$_2$(C$_1$-C$_3$)alkyl, O—SO$_2$phenyl or O—SO$_2$tolyl, although not devoid of dopamine agonist activity, are chiefly useful as intermediates for the preparation of the above mentioned more active agonists. All salts of these intermediates are useful in purification or synthetic procedures.

In the above formulas, the term "(C$_1$-C$_2$)-alkyl" includes methyl and ethyl and "(C$_1$-C$_3$)-alkyl" includes also n-propyl and isopropyl. The term "tolyl" includes p, m and o-tolyl.

The pharmaceutically-acceptable acid addition salts of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Compounds according to Ia above are named systematically as 4,4a,5,6,7,8,8a,9-octahydro-1H-pyrazolo[3,4-g]quinolines and those according to Ib as 4,4a,5,6,7,8,8a,9-octahydro-2H-pyrazolo[3,4-g]quinolines. These two structures represent a tautomeric pair when R$^2$ is H and the tautomers represented by the structures are in dynamic equilibrium. In addition, compounds represented by Formulas Ia and Ib above when R$^1$ is H have two chiral centers, the ring junction carbons at 8a and 4a. Thus, the compounds can occur as two racemates, ordinarily denominated as the trans-dl racemate and the cis-dl racemate. It is believed, however, according to the best evidence from $^{13}$C NMR spectral data, that the cyanoborohydride reduction process which introduces hydrogens at the quinoline bridge-head, a step in the synthetic procedure used to prepare the compounds of this invention, yields a trans-fused decahydroquinoline. While the arguments for the trans configuration based upon $^{13}$C NMR spectral data are compelling, an X-ray crystallographic investigation has also been carried out on a nicely crystalline enaminoketone in the decahydroquinoline series (VIII, R=CH$_3$). This x-ray analysis indicates clearly that the ring junction in the quinoline moiety is trans. Further operations on the decahydroquinoline molecule to condense a pyrazole ring thereon do not alter the configuration of the bridgehead hydrogens. Thus, only the trans racemate is prepared by the synthetic procedures to be disclosed hereinafter and the compounds of this invention are preferably represented as the trans-dl stereoisomers. The two trans stereoisomers of the 2H tautomer (R$^2$=H) can be represented as follows:

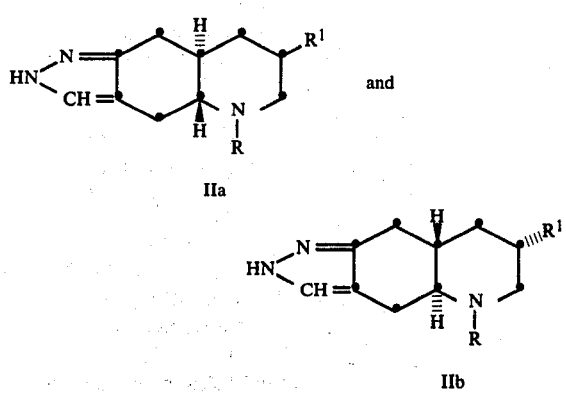

IIa and IIb represent a racemic pair. A similar racemic pair can be drawn for the 1H tautomer.

IIc

IId

IIc and IId also represent a racemic pair.

Resolution of these racemates into their optical antipodes can be accomplished by procedures known to those skilled in the art, and the individual trans-d and trans-l isomers are included within the scope of this invention.

In addition, when $R^1$ is other than H, a third chiral center is introduced at C-7. However, it is presently believed that the configuration of the C-7 group is chiefly beta relative to an alpha 8a hydrogen as in IIa. In the mirror image, IIb, $R^1$ is alpha with respect to 8a being beta. Thus, the trans-dl7-substituted octahydropyrazolo[3,4-g]quinolines of this invention are provided substantially as a single racemate or diastereoisomeric pair.

The following compounds illustrate the scope of our invention trans-dl-5-methyl-7-methoxymethyl-4,4a,5,6,7,8,8a,9-octahydro-2H-pyrazolo[3,4-g]quinoline,
trans-d-5-benzyl-7-ethoxycarbonyl-4,4a,5,6,7,8,8a,9-octahydro-1H-pyrazolo[3,4-g]quinoline hydrochloride,
trans-l-5-allyl-7-methylmercaptomethyl-4,4a,5,6,7,8-,8a,9-octahydro-2H-pyrazolo[3,4-g]quinoline maleate,
trans-dl-5-ethyl-4,4a,5,6,7,8,8a,9-octahydro-1H-pyrazolo[3,4-g]quinoline,
trans-dl-5-n-propyl-7-methylsulfonylmethyl-4,4a,5,6,7,8,8a,9-octahydro-1H-pyrazolo-[3,4-g]quinoline tartrate,
trans-d-5-methyl-7-cyanomethyl-4,4a,5,6,7,8,8a,9-octahydro-1H-pyrazolo[3,4-g]quinoline,
trans-dl-5-benzyl-7-carboxy-4,4a,5,6,7,8,8a,9-octahydro-2H-pyrazolo[3,4-g]quinoline mesylate,
trans-dl-1-methanesulfonyl-5-methyl-7-mesyloxymethyl-4,4a,5,6,7,8,8a,9-octahydro-1H-pyrazolo[3,4-g]quinoline mesylate,
trans-dl-5-ethyl-7-mesyloxymethyl-4,4a,5,6,7,8,8a,9-octahydro-1H-pyrazolo[3,4-g]quinoline sulfate,
trans-dl-5-methyl-4,4a,5,6,7,8,8a,9-octahydro-2H-pyrazolo[3,4-g]quinoline sulfate,
trans-dl-4,4a,5,6,7,8,8a,9-octahydro-1H-pyrazolo[3,4-g]quinoline sulfate,
trans-dl-2-p-tosyl-5-methyl-7-p-tosyloxymethyl-4,4a,5,6,7,8,8a,9-octahydro-2H-pyrazolo-[3,4-g]quinoline sulfate,
trans-dl-7-hydroxymethyl-4,4a,5,6,7,8,8a,9-octahydro-2H-pyrazolo[3,4-g]quinoline hydrochloride,
trans-dl-5-ethyl-7-chloromethyl-4,4a,5,6,7,8,8a,9-octahydro-1H-pyrazolo[3,4-g]quinoline tartrate,
trans-dl-5-n-propyl-7-carboamidomethyl-4,4a,5,6,7,8-,8a,9-octahydro-2H-pyrazolo[3,4-g]quinoline fumarate,
trans-dl-5-isopropyl-4,4a,5,6,7,8,8a,9-octahydro-2H-pyrazolo[3,4-g]quinoline,
trans-dl-5-benzyl-7-methoxycarbonyl-4,4a,5,6,7,8,8a,9-octahydro-1H-pyrazolo[3,4-g]quinoline,
trans-dl-7-methylmercaptomethyl-4,4a,5,6,7,8,8a,9-octahydro-1H-pyrazolo[3,4-g]quinoline,
trans-dl-5-n-propyl-7-methoxymethyl-4,4a,5,6,7,8,8a,9-octahydro-2H-pyrazolo[3,4-g]quinoline maleate,
trans-dl-5-ethyl-7-cyanomethyl-4,4a,5,6,7,8,8a,9-octahydro-2H-pyrazolo[3,4-g]quinoline,
trans-dl-5-allyl-4,4a,5,6,7,8,8a,9-octahydro-2H-pyrazolo[3,4-g]quinoline,
trans-dl-5-allyl-7-(α-phenylethoxycarbonyl-4,4a,5,6,7,8-,8a,9-octahydro-1H-pyrazolo[3,4-g]quinoline,
trans-dl-5-ethyl-7-hydroxymethyl-4,4a,5,6,7,8,8a,9-octahydro-2H-pyrazolo[3,4-g]quinoline.

For compounds listed above in which neither N-1 nor N-2 is substituted ($R^2$=H), it should be understood that each name also comprehends the other tautomer since an equilibrium mixture of the two tautomers is always present. The 2H tautomer apparently predominates in several of the tautomeric mixtures. In addition, the orientation of substituents is not given, nor is the configuration of the hydrogens at 4a and 8a, but it is understood that the hydrogens are trans to one another and that the 7 substituent is "trans" to the 8a hydrogen; i.e., when the 8a hydrogen is alpha, the 7 substituent is beta and when the 8a hydrogen is beta, the 7 substituent is oriented in the alpha configuration.

The compounds of this invention in which $R^1$ and $R^2$ are H are prepared according to the following procedure as outlined in Reaction Scheme I. In the Reaction Scheme, only one stereoisomer of the racemic pair, the 4aβ, 8aα isomer, has been drawn for convenience but it should be remembered that each decahydroquinoline and each octahydropyrazolo[3,4-g]quinoline exists as a racemate.

Reaction Scheme I

-continued
Reaction Scheme I

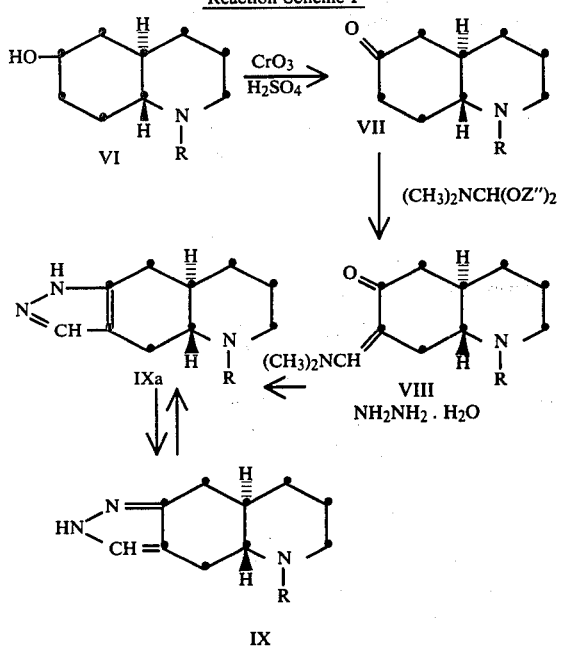

In the above reaction scheme, Z-CO is an acyl protecting group in which Z is ($C_1$–$C_3$)alkyl, ($C_2$–$C_3$)alkenyl, ($C_2$–$C_3$)alkynyl, ($C_5$–$C_6$)cycloalkyl, phenyl or substituted phenyl wherein the substituting group can be methyl, methoxy, chloro and the like at any position of the phenyl ring. Illustratively, Z-CO can be acetyl, propionyl, butyryl, propiolyl, acrylyl, benzoyl, p-toluyl, o-chlorobenzoyl, m-methoxybenzoyl etc.

Z″ is defined hereinbelow in the discussion of Reaction Scheme II. In accordance with Reaction Scheme I, 4-acyloxycyclohexanone prepared by the procedure of E.R.H. Jones and F. Sondheimer, *J. Chem. Soc.*, 615, (1949) for 4-benzoyloxycyclohexanone, is reacted with pyrrolidine in the presence of an acid catalyst to yield the pyrrolidine enamine. This enamine is in turn reacted with acrylamide to produce a mixture of dl-6-acyloxy-3,4,5,6,7,8-hexahydro-2(1H)quinolinone and dl-6-acyloxy-3,4,4a,5,6,7-hexahydro-2(1H)quinolinone represented by formula III, the dotted lines indicating the alternative positions of the double bond.

Next, the acidic nitrogen (acidic since it is alpha to a carbonyl group) is alkylated with an alkyl halide RX wherein R has the same meaning as hereinabove and X is a halogen such as Cl, Br or I, in the presence of sodium hydride to yield a mixture of dl-1-($C_1$–$C_3$) alkyl (or allyl or benzyl)-6-acyloxy-3,4,5,6,7,8-hexahydro-2(1H) quinolinone and its $\Delta^8$ isomer (IV). Reduction of this amide with lithium aluminum hydride or other suitable organometallic reducing agent yields a mixture of dl-1-($C_1$–$C_3$) alkyl (or allyl or benzyl)-6-hydroxy-1,2,3,4,5,6,7,8-octahydroquinoline and its $\Delta^8$ isomer. In this reaction mixture, conditions are encountered which also serve to hydrogenolyze the acyloxy group to a hydroxyl group at C-6. This dl-1-($C_1$–$C_3$) alkyl (or allyl or benzyl)-6-hydroxyoctahydroquinoline is next converted to an ammonium salt by treatment with hydrochloric acid, and the ammonium salt is then reduced with sodium cyanoborohydride to yield trans-dl-1-($C_1$–$C_3$) alkyl (or allyl or benzyl)-6-hydroxydecahydroquinoline (VI). Next, the trans-dl-1-($C_1$–$C_3$ alkyl, allyl, or benzyl)-6-hydroxydecahydroquinoline (VI) is oxidized using, preferably, chromium trioxide in acetic acid, to yield the corresponding 6-oxo compound (VII). This 6-oxo compound (VII) is reacted with dimethylformamide dimethylacetal to yield a 7-dimethylaminomethylene-6-oxo-derivative (VIII). Reaction of this derivative with hydrazine hydrate yields a tautomeric mixture of a tricyclic derivative, predominately trans-dl-5-[($C_1$–$C_3$)alkyl, allyl or benzyl)]-4,4a,5,6,7,8,8a,9-octahydro-2H-pyrazolo-[3,4-g]quinoline (IX) and its 1H tautomer (IXa) in smaller amount.

The compounds of this invention wherein R is $C_1$–$C_3$ alkyl or allyl, the dopamine agonists, can also be prepared from compounds in which R is benzyl. In this procedure, the benzyl group is removed by reductive cleavage or by treatment with cyanogen bromide to yield, eventually, a compound according to IX or IXa in which R is H progressing thru an intermediate when cyanogen bromide is used in which R is CN. This debenzylated compound can then be alkylated with a lower alkyl halide, or alternatively it may be reductively alkylated using acetaldehyde, acrolein or propionaldehyde in each instance with sodium cyanoborohydride to yield the desired N-alkyl or allyl derivative. The usual conditions for removing an N-benzyl group are hydrogen with a palladium-on-carbon catalyst or reaction with cyanogenbromide followed by reductive (Zn and acetic acid) cleavage of the N-cyano compound.

In the above reaction scheme, it is apparent from an inspection of the dl-trans-1 (substituted)-6-ketodecahydroquinoline (VII) that reaction with dimethylformamide dimethylacetal could take place at either C-5 or C-7 since both these carbons are alpha to the ketone group and thus available for reaction. The same x-ray crystallographic analysis of the enamine (VIII) discussed above clearly indicated that reaction had taken place at C-7 rather than C-5. Hence, the final tricyclic compounds, IX and IXa, are the linear pyrazolo[3,4-g]quinolines rather than the angular tricyclic compounds (which would be named as 4,4a,5,6,7,8,8a,9-octahydro-1H-pyrazolo[2,3-i]quinolines.

The compounds of this invention in which $R^1$ is other than H but $R^2$ remains H are prepared according to a slightly different procedure illustrated generally in Reaction Scheme II. As in Reaction Scheme I the procedure is exemplified with only (referring to the stereochemistry of the bridgehead) a single stereoisomer, the 4a$\beta$, 8a$\alpha$ isomer.

Reaction Scheme II

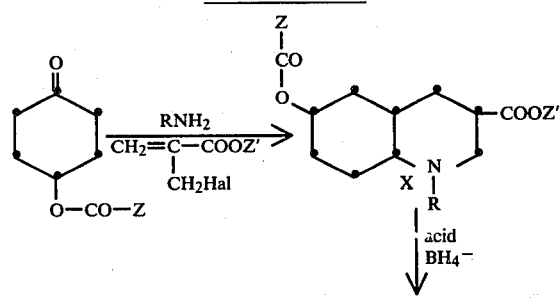

-continued
Reaction Scheme II

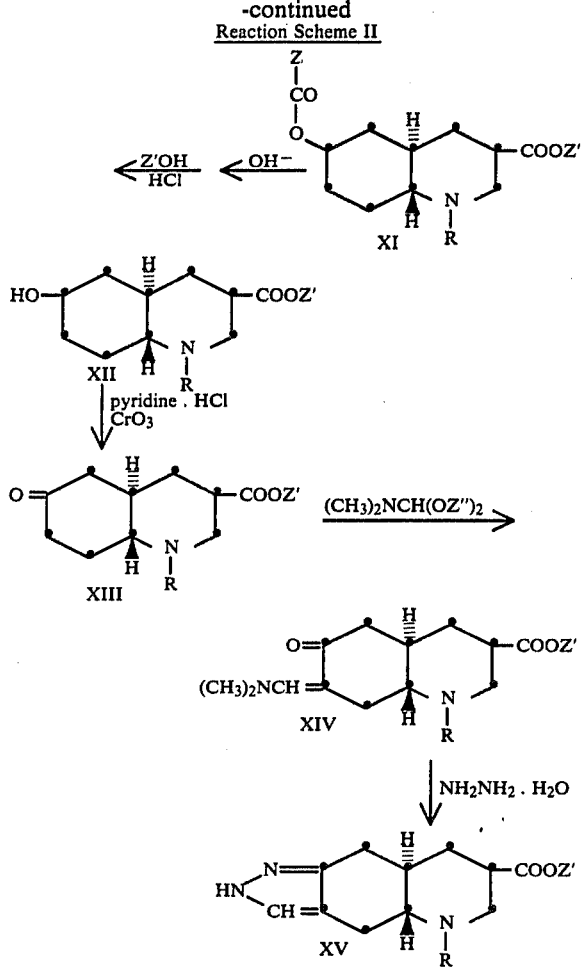

wherein Z and Z" have the same significance as in Reaction Scheme I, Hal is chloro or bromo and Z' is part of a readily hydrolyzable group Z'O-CO such as ($C_1$-$C_2$) alkyl, phenyl substituted ($C_1$-$C_2$) alkyl, illustratively benzyl, phenethyl, p-methoxybenzyl, methyl, ethyl etc.

In accordance with the Reaction Scheme II, a 4-acyloxycyclohexanone is reacted with an α-halomethylacrylate ester, for illustrative purposes, the ethyl ester and an amine, $RNH_2$, wherein R is $C_1$-$C_3$ alkyl, allyl or benzyl. The product of this reaction is a mixture of dl-1-substituted-3-ethoxycarbonyl-6-acyloxy-1,2,3,4,5,6,7,8,-octahydroquinoline and dl-1-substituted-3-ethoxycarbonyl-6-acyloxy-1,2,3,4,4a,5,6,7-octahydroquinoline represented by X in which the dotted line indicates the alternate positions of the double bonds. The hydrochloride salts of these isomers were prepared and the resulting mixture reduced with sodium cyanoborohydride to yield trans-dl-1-substituted-3-ethoxycarbonyl- 6-acyloxydecahydroquinoline (XI). Hydrolysis of this diester to yield a 6-hydroxy-3-carboxylic acid followed by reesterification of the carboxylic acid group with ethanol or other suitable alcohol in the presence of acid yields trans-dl-1-substituted-3-ethoxycarbonyl-6-hydroxydecahydroquinoline (XII). Oxidation of the hydroxy group with Sarett's Reagent (pyridine hydrochloride and chromium trioxide) produces the corresponding 6-oxo compound (XIII). Treatment of this 6-oxo derivative with a dimethylformamide acetal, preferably dimethylformamide dimethylacetal, results in reaction at C-7 (adjacent to the keto group) to give trans-dl-1-substituted-3-ethoxycarbonyl-6-oxo-7-(dimethylaminomethylene)-decahydroquinoline (XIV). Reaction of this derivative as in Reaction Scheme I above with hydrazine hydrate results in a mixture comprising trans-dl-5-substituted-7-ethoxycarbonyl-4,4a,5,6,7,8,8a,9-octahydro-1H-pyrazolo[3,4-g]quinoline and its 2H tautomer (represented by XV as a single stereoisomer). The compound can be isolated and purified as the free base or as the dihydrochloride salt, prepared according to conventional procedures.

Acetals of dimethylformamide useful in producing compound VIII in Reaction Scheme I and compound XIV in Reaction Scheme II have the general formula $(CH_3)_2N-CH-(OZ")_2$ in which Z" is ($C_1$-$C_8$)-alkyl, ($C_5$-$C_6$)cycloalkyl, ($C_3$-$C_4$)alkenyl, ($C_3$-$C_4$)-alkynyl and the like. We prefer to employ one of the commercially available acetals of dimethylformamide; i.e.; the dimethyl, diethyl, diisopropyl, dibutyl, dicyclohexyl, dipropyl or dineopentyl acetals.

In formula XV above, R is ($C_1$-$C_3$)alkyl, allyl or benzyl. The octahydropyrazolo[3,4-g]-quinoline of Formula XV represents a single tautomer, the 2H tautomer, and only one diastereoisomer. The mirror image of XV is also prepared and is included within the scope of this invention. We believe based upon analogy with the D-ergolines that the diastereoisomer XV is the isomer having dopamine agonist activity. The trans-dl racemate, which contains XV and its mirror image, is of course useful as a dopamine agonist, even though most of the desired activity resides in one of its component stereoisomers.

Intermediates described in Reaction Schemes I and II, having the following structures, form a part of this invention

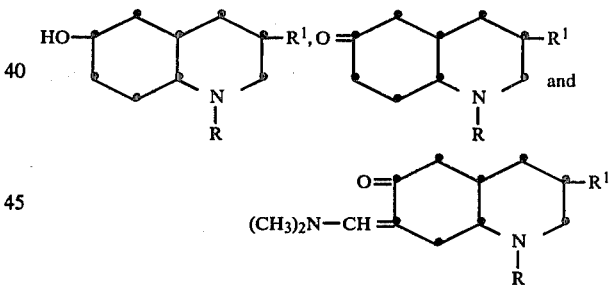

wherein R is ($C_1$-$C_3$)alkyl, allyl or benzyl and $R^1$ is COOZ' wherein Z' is ($C_1$-$C_2$)alkyl or phenyl-substituted ($C_1$-$C_2$)alkyl. These intermediates are prepared by the methods set forth in those reaction schemes, in the accompanying detailed description and in the Examples which follow.

Compounds according to XV above in which R is ethyl, allyl or n-propyl can be prepared by two different procedures. First, the amine, $RNH_2$, used in preparing X can be ethyl, n-propyl or allyl thus introducing the group directly. Alternatively a compound according to XV in which R is methyl or benzyl can be transformed into a compound in which R is H by removing the methyl or benzyl group by reaction with cyanogen bromide. The intermediate 5-cyano (R is CN) derivative can be reductively cleaved (zinc plus acetic acid) to yield a compound in which R is H. In addition, the benzyl group can be removed by hydrogenation with palladium-on-carbon to yield those intermediates in which R=H. Akylation of the secondary amine can be accomplished by reaction with an alkyl halide—RCl, RBr or RI. Alternatively, the secondary amine group can be reacted with acetaldehyde, acrolein, or propionaldehyde under reducing conditions (NaBH$_3$CN) to yield an N-ethyl, N-allyl or N-n-propyl derivative.

The dopamine agonists of this invention, those compounds in which R$^1$ is CH$_2$X wherein X is CN, OCH$_3$, SCH$_3$, SO$_2$CH$_3$ or CO-NH$_2$, are prepared from compound XV according to Reaction Scheme III below

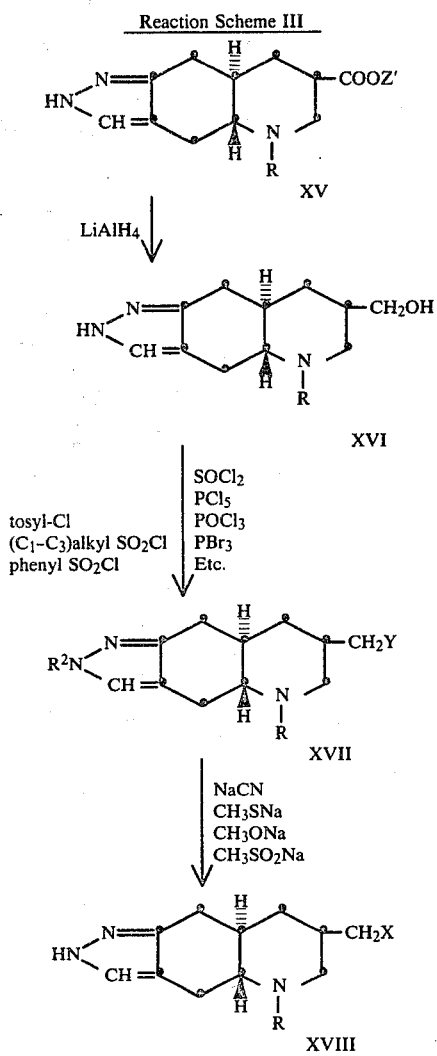

wherein Y is a "leaving" group: Cl, Br, OSO$_2$phenyl, O-tosyl or SO$_2$(C$_1$-C$_3$)alkyl, R$^2$ is H, SO$_2$phenyl, tosyl or SO$_2$(C$_1$-C$_3$)alkyl, and X is CN, SCH$_3$, OCH$_3$ or SO$_2$CH$_3$.

In Reaction Scheme III, as before, only one tautomer, the 2H tautomer, is illustrated. Furthermore, the 2H tautomer exists as a racemate and only one diastereoisomer is illustrated, the 4aβ, 7β, 8aα isomer. The mirror image compound is, of course, also produced since it constitutes half of the starting material, XV. The trans-dl racemates of XVIII are useful as dopamine agonists because of their content of active agonist. The intermediate racemates, XV, XVI and XVII are useful in that each contains a diastereoisomer which can be chemically transformed to an active dopamine agonist.

According to Reaction Scheme III, a trans-dl-5-substituted-4,4a,5,6,7,8,8a,9-octahydro-2H-pyrazolo[3,4-g]quinoline-7-carboxylate ester is reduced with a metal hydride reducing agent such as LiAlH$_4$ to a pyrazolo[3,4-g]quinoline with a 7-hydroxymethyl group (XVI). The thus-produced hydroxyl is next replaced with a "leaving group"; i.e., a group readily displaced by a nucleophilic reagent, including chlorine, bromine and the halogen-like esters, tosylate (usually p-toluene sulfonate), alkyl sulfonate, benzene sulfonate etc. to produce a compound of structure XVII. The Cl or Br leaving groups are introduced by reaction with PCl$_3$, SOCl$_2$, PCl$_5$, POCl$_3$, PBr$_3$ and the like, and the sulfonate esters by reaction with the corresponding sulfonyl chloride. This latter reaction results also in reaction on the pyrazole nitrogen to produce the compounds of this invention in which R$^2$ is (C$_1$-C$_3$)alkyl SO$_2$, tosyl or phenyl SO$_2$. Compounds in which R$^2$ is other than H are no longer tautomeric. The percent of 2-substituted pyrazolo[3,4-g]quinoline versus the percent of the 1-substituted derivative, in fact, gives an indication of the percent of each tautomer prior to reaction with the sulfonyl chloride. The amount of XVII in which R$_2$ is H compared with the amount in which R$_2$ is a sulfonyl group depends on the amount of sulfonyl halide employed. Obviously, two molar or greater amount of sulfonyl halide will produce a 2(or 1)-sulfonyl-7-sulfonyloxymethyl derivative, but quantities less than two moles produce a mixture of the 2(or 1)-sulfonyl-7-sulfonyloxymethyl derivative and the 7-sulfonyloxymethyl tautomeric mixture unsubstituted in the pyrazole ring. Reaction of XVII with sodium methylate, methylmercaptan sodium salt, sodium cyanide, sodium methanesulfinate or other basic salts of methanol, methylmercaptan etc. yields compounds according to Formula Ia, Ib, Ic or Id in which X is SCH$_3$, OCH$_3$, CN or SO$_2$CH$_3$. These basic reaction conditions also serve to hydrolyze the sulfonyl group in the pyrazole ring, if any, to produce a tautomeric mixture XVIII (of which only the 2-tautomer is illustrated). Compounds in which X is CONH$_2$ are prepared by hydration of the corresponding cyano compound.

This invention is further illustrated by the following specific examples.

EXAMPLE 1

Preparation of trans-dl-4,4a,5,6,7,8,8a,9-octahydro-1H and 2H-pyrazolo[3,4-g]quinoline A reaction mixture was prepared from 65 g. of 4-benzoyloxycyclohexanone, 38 ml. of pyrrolidine, a few crystals of p-toluenesulfonic acid monohydrate, and 1000 ml. of benzene. The reaction mixture was heated to refluxing temperature under a nitrogen atmosphere for one hour in an apparatus equipped with a Dean-Stark water trap. The reaction mixture was then cooled and the volatile constituents removed by evaporation in vacuo. The residue, comprising the pyrrolidine enamine of 4-benzoyloxycyclohexanone formed in the above reaction, was dissolved without further purification in 1000 ml. of dioxane. 64 g. of acrylamide were added. This new reaction mixture was heated under a nitrogen atmosphere at reflux temperature for two days after which time it was cooled and the volatile constituents removed by evaporation in vacuo. The reaction mixture was diluted with ethyl acetate and the ethyl acetate layer separated, washed first with water and then with saturated aqueous sodium chloride. The ethyl acetate layer was dried and the volatile constituents removed by evaporation in vacuo. The resulting residue, comprising a mixture of 2-oxo-6-benzoyloxy-3,4,5,6,7,8-hexahydroquinoline and 2-oxo-6-benzoyloxy-3,4,4a,5,6,7,-hexahydroquinoline formed in the above reaction, was dissolved in chloroform and the chloroform solution chromatographed over florisil. Chloroform containing increasing amounts of ethanol (0 to 2 percent) was used as the eluant. Fractions found to contain 2-oxo-6-benzoyloxy-3,4,5,6,7,8-hexahydroquinoline and its $\Delta^{8(8a)}$ isomer by thin-layer chromatography were combined and the solvent removed therefrom in vacuo. The resulting residue was crystallized by triturating with hexane to yield a crystalline mixture of 6-benzoyloxy-3,4,5,6,7,8-hexahydro-1H-quinolin-2-one and the corresponding 3,4,4a,5,6,7-hexahydro derivative. The mixture melted in the range 130°–150° C. after recrystallization from an ether-hexane solvent mixture.

Analysis: Calculated: C, 70.83; H, 6.32; N, 5.16. Found: C, 71.05; H, 6.19; N, 5.33.

NMR of the product isolate above indicated that the mixture contained about 60 percent of 6-benzoyloxy-3,4,5,6,7,8-hexahydro-1H-quinolin-2-one and 40% of the 3,4,4a,5,6,7,-hexahydro isomer.

A mixture of 2-oxo-6-benzoyloxy-3,4,5,6,7,8,-hexahydroquinoline and its $\Delta^{8(8a)}$ isomer obtained from 65 g. of 4-benzoyloxycyclohexanone as above without further purification was dissolved in a mixture of 300 ml. of tetrahydrofuran (THF) and 300 ml. of dimethylformamide. 14 g. of sodium hydride were added, thus forming the sodium salt of the quinoline. This mixture was stirred at ambient temperature for about 20 minutes under a nitrogen atmosphere after which time 55 g. of benzyl bromide in 75 ml. of THF were slowly added over a 10 minute period. The reaction mixture was stirred for an additional hour in the range 32°–45° C. and was then diluted with water. The aqueous mixture was extracted with ethyl acetate. The ethyl acetate extract was separated, washed with water and with saturated aqueous sodium chloride, and then dried. Evaporation of the ethyl acetate yielded a mixture of 1benzyl-2-oxo-6-benzoyloxy-3,4,5,6,7,8-hexahydroquinoline and 1-benzyl-2-oxo-6-benzoyloxy-3,4,4a,5,6,7-hexahydroquinoline; yield=106 g.

106 g. of the above mixture were dissolved in 1 l. of THF and the solution cooled in an ice-water bath. 40 g. of lithium aluminumhydride were added thereto in portions. After the addtion had been completed, the reaction mixture was heated to refluxing temperature under a nitrogen atmosphere for about 4 hours. The reaction mixture was then cooled and excess lithium aluminumhydride destroyed by the addition of ethyl acetate. 10 percent aqueous sodium hydroxide was added to decompose any organometallic compounds present in the mixture. At this point, the reaction mixture was diluted with water. The resulting aqueous mixture was extracted several times with chloroform. The chloroform extracts were separated and combined. The combined extracts were washed with saturated aqueous sodium chloride and then dried. Evaporation of the chloroform yielded a residue comprising a mixture of 1-benzyl-6-hydroxy-1,2,3,4,5,6,7,8-octahydroquinoline and 1-benzyl-6-hydroxy-1,2,3,4,4a,5,6,7-octahydroquinoline. (Both the 2-oxo group and the 6-benzoyloxy group reacted with the lithium aluminum hydride to yield an octahydroquinoline with a free alcohol at C-6). The mixture of compounds thus obtained was dissolved in ether, the ethereal solution cooled, and gaseous anhydrous hydrogen chloride passed into the solution, thus forming the hydrochloride salts of the quinoline isomers. The quinoline hydrochlorides were insoluble and were separated by decantantation of the ether. The residual salts were dissolved in 100 ml. of methanol and 400 ml. of THF. The solution was cooled and 30 g. of sodium cyanoborohydride added thereto in portions. After the addition had been completed, the cooling bath was removed and the reaction mixture stirred at ambient temperature for 1.25 hours, after which time it was poured into a mixture of 1 N aqueous hydrochloric acid and ice. The acidic solution was extracted with ether, and the ether extract discarded. The acidic solution was then made basic with 10 percent aqueous sodium hydroxide and the alkaline mixture extracted several times with a chloroform-isopropanol solvent mixture. The organic extracts were combined, and the combined extracts washed with saturated aqueous sodium chloride and then dried. Evaporation of the solvent yielded trans-dl-1-benzyl-6-hydroxydecahydroquinoline formed in the above reaction; yield=53.6 g. Total yield in 6 steps was 73 percent based upon recovered 4-benzoyloxycyclohexanone starting material.

53 g. of trans-dl-1-benzyl-6-hydroxydecahydroquinoline were dissolved in 1.5 l. of methylene dichloride and the solution cooled in an ice-water bath. 50 g. of cyanogen bromide were added and the resulting mixture stirred at room temperature for 15 hours. The reaction mixture was washed successively with 1 N aqueous hydrochloric acid and water, and was then dried. Evaporation of the solvent yielded a residue containing trans-dl-1-cyano-6-hydroxydecahydroquinoline formed in the above reaction. The residue was dissolved in chloroform and the chloroform solution chromatographed over 300 g. of florisil using chloroform containing increasing amounts (0–2%) of methanol as the eluant. Fractions shown by TLC to contain the desired cyano compound were combined and the solvent removed from the combined fraction by evaporation in vacuo. trans-dl-1-cyano-6-hydroxydecahydroquinoline thus prepared weighed 22.5 g.

22.5 g. of trans-dl-1-cyano-8-hydroxydecahydroquinoline were dissolved in 1200 ml. of methylene dichloride. 33 g. of pyridine hydrochloride:chromium trioxide (Sarett's Reagent) were added. The reaction mixture was stirred at room temperature under nitrogen for about 6 hours, and was then filtered. The filtrate was concentrated in vacuo and the concentrate chromatographed over 300 g. of florisil using chloroform containing 1 percent methanol as the eluant. Fractions shown by TLC to contain trans-dl-1-cyano-6-oxodecahydroquinoline formed in the above reaction were combined and the combined fractions evaporated to dryness in vacuo. Recrystallization of the resulting residue from an ether-chloroform solvent mixture yielded trans-dl-1-cyano-6-oxodecahydroquinoline melting at 86°–8° C.; yield=18.9 g.

Analysis:Calculated: C, 67.39; H, 7.92; N, 15.72. Found: C, 67.15; H, 7.75; N, 15.46.

17.6 g. of trans-dl-1-cyano-6-oxodecahydroquinoline were dissolved in 200 ml. of benzene to which 100 g. of the dimethylacetal of dimethylformamide had been added. The reaction mixture was heated to refluxing temperature under nitrogen for about 20 hours and was then cooled. Evaporation of the solvent in vacuo yielded a residue comprising trans-dl-1-cyano-6-oxo-7-dimethylaminomethylenedecahydroquinoline formed in the above reaction. The compound was purified by chromatography over 300 g. of florisil using chloroform containing increasing amounts (0-2%) of methanol as the eluant. 10.2 g. of trans-dl-1-cyano-6-oxo-7-dimethylaminomethylenedecahydroquinoline melting at 159°-163° C. were obtained. The compound was crystallized from toluene to yield crystals melting at 162°-4° C.

Analysis:Calculated: C, 66.92; H, 8.21; N, 18.01. Found: C, 67.14; H, 8.16; N, 18.04.

10.2 g. of trans-dl-1-cyano-6-oxo-7-dimethylaminomethylenedecahydroquinoline were dissolved in 400 ml. of methanol. 2.8 g. of 85 percent hydrazine were added and the subsequent reaction mixture stirred for about 1 day under a nitrogen atmosphere. The volatile constituents were then removed by evaporation in vacuo. The residue was dissolved in chloroform and the chloroform solution chromatographed over 150 g. of florisil using chloroform containing increasing amounts (2-5%) of methanol as the eluant. Fractions shown by TLC to contain the desired octahydropyrazoloquinoline were combined and the solvent evaporated therefrom to dryness; yield = 6.3 g. Recrystallization of the residue from ethanol yielded a mixture of trans-dl-5-cyano-4,4a,5,6,7,8,8a,9-octahydro-2H-pyrazolo[3,4-g]quinoline and its 1H tautomer melting at 193°-5° C.

Analysis: Calculated: C, 65.32; H, 6.98; N, 27.70 Found: C, 65.48; H, 6.80; N, 27.64

A reaction mixture prepared from 860 mg of trans-dl-5-cyano-4,4a,5,6,7,8,8a,9-octahydro-1H and 2H-pyrazolo[3,4-g]quinoline, 5 g. of zinc dust, 10 ml. of water and 50 ml. of acetic acid. The mixture was heated to refluxing temperature under a nitrogen atmosphere for 18.5 hours after which time it was filtered and the filtrate poured over ice. The resulting aqueous mixture was then made basic with 14 N ammonium hydroxide and the resulting alkaline aqueous layer extracted several times with a chloroform-isopropanol solvent mixture. The organic extracts were combined and the combined extracts washed with saturated aqueous sodium chloride and then dried. Evaporation of the solvent yielded a residue comprising trans-dl-4,4a,5,6,7,8,8a,9-octahydro-2H-pyrazolo[3,4-g]quinoline and the 1H tautomer formed in the above reaction. The residue was dissolved in ethanol and 0.70 ml. of 12 N aqueous hydrochloric acid added thereto. The mixture of trans-dl-4,4a,5,6,7,8,8a,9-octahydro-2H-pyrazolo[3,4-g]quinoline and the 1H-tautomer dihydrochlorides formed as above melted at 284°-7° C.; yield = 780 mg.

Analysis:Calculated: C, 48.01; H, 6.85; N, 16.80. Found: C, 48.07; H, 7.05; N, 16.83.

EXAMPLE 2

Preparation of trans-dl-5-n-Propyl-4,4a,5,6,7,8,8a,9-octahydro-1H and 2H-pyrazolo[3,4-g]quinoline A reaction mixture was prepared from 6.3 g. of a mixture of trans-dl-5-cyano-4,4a,5,6,7,8,8a,9-octahydro-2H-pyrazolo[3,4-g]quinoline and its 1H-tautomer (prepared by the procedure of the above example), 30 g. of zinc dust, 375 ml. of acetic acid and 75 ml. of water. The reaction mixture was heated to refluxing temperature under nitrogen for 16 hours after which time it was filtered and the filtrate poured over ice. The resulting aqueous mixture was made basic by the addition of 14 N aqueous ammonium hydroxide and the alkaline layer extracted several times with a chloroform-isopropanol solvent mixture. The organic extracts were combined, the combined extracts washed with saturated aqueous sodium chloride and then dried. Evaporation of the solvent yielded a residue comprising trans-dl-4-4a,5,6,7,8,8a,9-octahydro-2H-pyrazolo[3,4-g]quinoline and its 1H-tautomer formed in the above reaction. The residue was dissolved in 500 ml. of methanol to which was added 1.9 g. of sodium cyanoborohydride. Next 20 ml. of propionaldehyde were added and the resulting mixture stirred at ambient temperature under a nitrogen atmosphere for 28 hours. The reaction mixture was then poured into 1 N aqueous hydrochloric acid. The aqueous layer was extracted with ether and the ether extracts discarded. The aqueous layer was then made basic by the addition of an excess of 14 N aqueous ammonium hydroxide and the resulting alkaline layer extracted several times with a chloroform-isopropanol solvent mixture. The organic extracts were combined and the combined extracts washed with saturated aqueous sodium chloride and then dried. Evaporation of the solvent yielded a residue comprising trans-dl-5-n-propyl-4,4a,5,6,7,8,8a,9-octahydro-1H and 2H-pyrazolo[3,4-g]quinoline formed in the above reaction. Mass spectrum: M+ = 219.

The residue was dissolved in 100 ml. of boiling acetone to which were added 5 ml. of 12 N aqueous hydrochloric acid in dropwise fashion. The mixture was cooled and the dihydrochlorides of trans-dl-5-n-propyl-4,4a,5,6,7,8,8a,9-octahydro-1H and 2H-pyrazolo[3,4-g]quinoline thus formed separated by filtration; yield = 4.6 g.; m.p. = 250°-7° C.

Analysis:Calculated: C, 53.43; H, 7.93; N, 14.38; Cl, 24.26. Found: C, 53.15; H, 7.91; N, 14.47; Cl, 24.33

Using the above procedure, 1.2 g. of a mixture of trans-dl-5-cyano-4,4a,5,6,7,8,8a,9-octahydro-2H-pyrazolo[3,4-g]quinoline and its mixture of 1H-tautomer were reacted with zinc dust and acetic acid to form a mixture of trans-dl-4,4a,5,6,7,8,8a,9-octahydro-2H-pyrazolo[3,4-g]quinoline and its 1H tautomer which was isolated as a residue. This residue dissolved in 50 ml. of DMF to which were added 1.7 g. of potassium carbonate. Next, 0.6 ml. of n-propyl iodide were added and the resulting mixture stirred at ambient temperature for about 4 hours under a nitrogen atmosphere. The reaction mixture was diluted with water and the resulting aqueous mixture extracted several times with ethyl acetate. The ethyl acetate extracts were combined and the combined extracts washed successively with water and saturated aqueous sodium chloride and were then dried. Evaporation of the ethyl acetate yielded a residue comprising trans-dl-5-n-propyl-4,4a,5,6,7,8,8a,9-octahydro-2H-pyrazolo[3,4-g]quinoline and its 1H tautomer which was purified by chromatography over 30 g. of florisil using chloroform containing increasing amounts (2-10%) of methanol as the eluant. Fractions shown by TLC to contain trans-dl-5-n-propyl-4,4a,5,6,7,8,8a,9-octahydro-2H and 1H-pyrazolo[3,4-g]quinoline were combined and the combined extracts evaporated to dryness to yield 0.28 g. of trans-dl-5-n-propyl-4,4a,5,6,7,8,8a,9-octahydro-2H-pyrazolo[3,4-g]quinoline and its 1H tautomers. The residue was dissolved in ethanol to which was added 0.16 ml. of 12 N aqueous hydrochloric acid, thus forming the dihydrochlorides of trans-dl-5-n-propyl-4,4a,5,6,7,8,8a,9-octahydro-2H-pyrazolo[3,4-g]quinoline and the 1H tautomer. The reaction mixture was concentrated in vacuo and the concentrate diluted with ether. A mixture of trans-dl-5-n-propyl-4,4a,5,6,7,8,8a,9-octahydro-1H and 2H- pyrazolo[3,4-g]quinoline dihydrochloride crystallized and was separated by filtration; m.p.=276°-8° C.

EXAMPLE 3

Preparation of trans-dl-5-n-Propyl-7-ethoxycarbonyl-4,4a,5,6,7,8,8a,9-octahydro-1H and 2H-pyrazolo[3,4-g]quinoline A mixture of 10 ml. of n-propyl amine and 400 ml. of toluene were cooled in an ice-water bath. A solution of 16.5 g. of ethyl α-(bromomethyl)acrylate in 50 ml. of toluene was added thereto in dropwise fashion. The resulting mixture was stirred with cooling for about 25 minutes. Next, a solution of 11 g. of 4-benzoyloxycyclohexanone in 75 ml. of toluene was added in dropwise fashion. This new mixture was heated under a nitrogen atmosphere to refluxing temperature for about 23 hours. The reflux condenser was equipped with a Soxhlet extractor containing a 5A sieve to remove water. Next the reaction mixture was cooled and the cooled mixture filtered. Evaporation of the filtrate yielded a residue comprising a mixture of 1-n-propyl-3-ethoxycarbonyl-6-benzoyloxy-1,2,3,4,5,6,7,8-octahydroquinoline and 1-n-propyl-3-ethoxycarbonyl-6-benzoyloxy-1,2,3,4,4a,5,6,7-octahydroquinoline. The residue was dissolved in an ether-chloroform solvent mixture and the resulting solution saturated with gaseous hydrogen chloride while maintaining the temperature in the range 0°-5° C. The solvent was decanted from the crystalline hydrochloride salts thus formed. The salts were dissolved in 100 ml. of methanol. 300 ml. of THF were added and the resulting solution cooled in an ice-water bath. 15 g. of sodium cyanoborohydride were added in portions to the stirred and cooled reaction mixture. After the addition had been completed, the reaction mixture was stirred for another 1.25 hours after which time it was diluted with aqueous sodium bicarbonate. The aqueous alkaline mixture was extracted several times with ethyl acetate. The ethyl acetate extracts were combined and the combined extracts washed with saturated aqueous sodium chloride solution and then dried. Evaporation of the solvent yielded trans-dl-1-n-propyl-3-ethoxycarbonyl-6-benzoyloxydecahyroquinoline. hydroquinoline. The compound was dissolved in a mixture of 400 ml. of methanol and 100 ml. of 2 N aqueous sodium hydroxide. This mixture was stirred at ambient temperature under a nitrogen atmosphere for 64 hours after which time the volatile constituents were removed by evaporation in vacuo. The resulting residue was suspended in 800 ml. of ethanol and 15 ml. of 12 N aqueous hydrochloric acid. The esterification mixture was heated to refluxing temperature and about 300 ml. of solvent removed by distillation. 300 ml. of additional ethanol were added and the reaction mixture heated to refluxing temperature for 26 hours in an apparatus equipped with a Soxhlet trap containing a 3A sieve. The reaction mixture was cooled, diluted with aqueous sodium bicarbonate and the alkaline mixture extracted several times with chloroform. The chloroform extracts were combined and the combined extracts washed with saturated aqueous sodium chloride and then dried. Evaporation of the chloroform yielded 10.3 g. of a residue comprising trans-dl-1-n-propyl-3-ethoxycarbonyl-6-hydroxydecahydroquinoline formed in the above hydrolysis after chromatography over 150 g. of florisil using chloroform containing increasing amounts (2-10%) of methanol as the eluant.

A solution was prepared from 8.8 g. of trans-dl-1-n-propyl-3-ethoxycarbonyl-6-hydroxydecahydroquinoline and 400 ml. of methylene dichloride. 4.1 g. of sodium acetate were added. Next, 10.8 g. of pyridine hydrochloride:chromium trioxide were added and the resulting mixture stirred for about 22 hours. The reaction mixture was filtered and the filtrate concentrated in vacuo. The resulting concentrate was dissolved in chloroform and the chloroform solution chromatographed over 150 g. of florisil using chloroform containing increasing amounts (1-2%) of methanol as the eluant. Fractions shown by thin-layer chromatography to contain trans-dl-1-n-propyl-3-ethoxycarbonyl-6-oxodecahydroquinoline formed in the above reaction were combined and the solvent removed from the combined extracts to yield 3.48 g. of the 6-oxo compound as a residue. The 6-oxo compound was dissolved in 100 ml. of toluene containing an added 25 ml. of the dimethylacetal of dimethylformamide. The resulting mixture was heated to refluxing temperature under a nitrogen atmosphere for 44 hours and was then allowed to remain at room temperature for an additional 4 days. Volatile constituents were removed by evaporation in vacuo and the residue, comprising trans-dl-1-n-propyl-3-ethocycarbonyl-6-oxo-7-(dimethylaminomethylene)-decahydroquinoline formed in the above reaction, was purified by chromatographing a chloroform solution of the compound over florisil using chloroform containing increasing amounts (2-5%) of methanol as the eluant. Fractions shown by TLC to contain the desired 7-dimethylaminomethylene compound were combined and the solvent evaporated therefrom in vacuo.

A solution was prepared from 2.24 g. of trans-dl-1-n-propyl-3-ethoxycarbonyl-6-oxo-7-dimethylaminomethylene decahydroquinoline and 150 ml. of ethanol. 0.45 ml. of hydrazine hydrate were added and the resulting mixture stirred at ambient temperature for about 17 hours. The reaction mixture was evaporated to dryness in vacuo. The residue containing a mixture of trans-dl-5-n-propyl-7-ethoxycarbonyl-4,4a,5,6,7,8,8a,9-octahydro-2H-pyrazolo[3,4-g]quinoline and trans-dl-5-n-propyl-7-ethoxycarbonyl-4,4a,5,6,7,8,8a,9-octahydro-1H-pyrazolo[3,4-g]quinoline was dissolved in chloroform and the resulting solution chromatographed over 35 g. of florisil using chloroform containing 2 percent methanol as an eluant. Fractions shown to contain the desired pyrazoloquinoline by TLC were combined and the solvent evaporated therefrom in vacuo. Recrystallization from a mixture of ether and hexane yielded trans-dl-5-n-propyl-7-ethoxycarbonyl-4,4a,5,6,7,8,8a,9-octahydro-2H-pyrazolo[3,4-g]quinoline and its 1H tautomer melting at 125-7° C.

Analysis: Calculated: C, 65.95; H, 8.65; N, 14.42.
Found: C, 65.75; H, 8.42; N, 14.16.

EXAMPLE 4

Preparation of trans-dl-5-n-Propyl-7-hydroxymethyl-4,4a,5,6,7,8,8a,9-octahydro-1H and 2H-pyrazolo[3,4-g]quinoline A mixture of trans-dl-5-n-propyl-7-ethoxycarbonyl-4,4a,5,6,7,8,8a,9-octahydro-2H-pyrazolo[3,4-g]guinoline dihydrochloride and the dihydrochloride salt of the 1H tautomer (3.7 millimoles) was suspended in 200 ml. of THF. 1 g. of lithium aluminumhydride was added thereto in portions. The consequent reaction mixture was stirred at ambient temperature under a nitrogen atmosphere for about 16 hours, and was then cooled. Ethyl acetate and 10 percent aqueous sodium hydroxide were added thereto seriatium to react with any excess lithium aluminumhydride and to decompose organometallic compounds present. The reaction mixture so treated was then diluted with water and the aqueous mixture extracted several times with a chloroform-isopropanol solvent mixture. The organic layers were separated and combined. The combined layers were washed with saturated aqueous sodium chloride and then dried. Evaporation of the solvent yielded a mixture of trans-dl-5-n-propyl-7-hydroxymethyl-4,4a,5,6,7,8-,8a,9-octahydro-2H-pyrazolo[3,4,-g]quinoline and its 1H tautomer. The residue was dissolved in ethanol to which was added 0.2 ml. of 12 N aqueous hydrochloric acid. Evaporation of the volatile constituents yielded a residue comprising trans-dl-5-n-propyl-7-hydroxymethyl-4,4a,5,6,7,8,8a,9-octahydro-2H and 1H-pyrazolo[3,4,-g]quinoline dihydrochlorides. The residue was dissolved in a mixture of methanol and acetone to yield crystals melting at 270°-5° C. with decomposition; yield =350 mg.

The above reaction was repeated with 1.55 g. of trans-dl-5-n-propyl-7-ethoxycarbonyl-4,4a,5,6,7,8,8a,9-octahydro-2H-pyrazolo[3,4-g]-quinoline in THF being reduced with an excess of lithium aluminumhydride. The produce of the reaction, trans-dl-5-n-propyl-7-hydroxymethyl-4,4a,5,6,7,8,8a,9-octahydro-1H and 2H -pyrazolo[3,4-g]quinoline, was crystallized from a mixture of chloroform and ethanol to yield crystalline material melting at 167°-9° C.

Analysis: Calculated: C, 67.43; H, 9.30; N, 16.85; Found: C, 67.21; H, 9.13; N, 16.62.

EXAMPLE 5

Preparation of trans-dl-2-methanesulfonyl-5-n-propyl-7-mesyloxymethyl-4,4a,5,6,7,8,8a,9-octahydro-2H-pyrazolo[3,4-g]quinoline A suspension was prepared from 1 millimole of trans-dl-5-n-propyl-7-hydroxymethyl-4,4a,5,6,7,8,8a,9-octahydro-1H and 2H-pyrazolo[3,4-g]quinoline in 100 ml. of pyridine. 1 ml. of methanesulfonyl chloride (mesyl chloride) was added and the resulting mixture left over night at ambient temperature. The mixture was diluted with dilute aqueous ammonium hydroxide and the resulting alkaline layer extracted several times with chloroform. The chloroform extracts were combined and the combined extracts washed with saturated aqueous sodium chloride and then dried. Evaporation of the solvent yielded a solid residue. A chloroform solution of the residue was chromatographed over 30 g. of florisil using chloroform containing increasing amounts (1-2%) of methanol as the eluant. Fractions shown by TLC to contain trans-dl-2-methanesulfonyl-5n-propyl-7-mesyloxymethyl-4,4a,5,6,7,8,8a,9-octahydro-2H-pyrazolo[3,4-g]quinoline were combined and the solvent was removed therefrom by evaporation. trans-dl-2-Methanesulfonyl-5-n-propyl-7-mesyloxymethyl-4,4a,5,6,7,8,8a,9-octahydro-2H-pyrazolo[3,4-g]quinoline melted 152°-4° C. after recrystallization from ether.

Analysis: Calculated: C, 47.39; H, 6.71; N, 10.36; S, 15.81. Found: C, 47.60; H 6.71; N, 10.32; S, 15.69.

A second fraction was obtained from the chromatography was shown by NMR to be a 2:1 mixture of trans-dl-5-n-propyl-7-mesyloxymethyl-2-methanesulfonyl-4,4a,5,6,7,8,8a,9-octahydro-2H-pyrazolo-[3,4-g]quinoline and its 1-methanesulfonyl-1H isomer.

EXAMPLE 6

Preparation of trans-dl-5-n-Propyl-7-methylmercaptomethyl-4,4a,5,6,7,8,8a,9-octahydro-1H and 2H-pyrazolo[3,4-g]quinoline 1 g. of methylmercaptan was dissolved in 40 ml. of dimethylformamide. The solution was cooled in an ice-water bath. About 1 g. of sodium hydride (as a 50% suspension in mineral oil) was added thereto in portions. The cooling bath was removed and a solution containing 0.4 g. of trans-dl-2-methanesulfonyl-5-n-propyl-7-mesyloxymethyl-4,4a,5,6,7,8,8a,9-octahydro-2H-pyrazolo[3,4-q]quinoline containing some trans-dl-1-methanesulfonyl-5-n-propyl-7-mesyloxymethyl-4,4a,5,6,7,8,8a,9-octahydro-1H-pyrazolo[5,4-g]quinoline in 10 ml. of DMF prepared as in Example 5 was added. The reaction mixture was stirred at ambient temperature for about 5 hours and was then diluted with water. The aqueous mixture was extracted several times with ethyl acetate. The ethyl acetate extracts were separated and combined. The combined extracts were washed with water and with saturated aqueous sodium chloride and then dried. Evaporation of the solvent yielded an oily residue comprising trans-dl-5-n-propyl-7-methylmercaptomethyl-4,4a,5,6,7,8,8a,9-octahydro-1H and 2H-pyrazolo[3,4,-g]quinoline; yield=0.17 g. The residue was dissolved in ethanol and attempts made to prepare both the hydrochloride and the oxalate salts. Both salts initially turned out to be noncrystalline. The free bases were then recovered from the noncrystalline oxalate by dissolving the oxalate in water, adding base and extracting the mixture with ether. trans-dl-5-n-Propyl-7-methylmercaptomethyl-4,4a,5,6,7,8,8a,9-octahydro-1H and 2H-pyrazolo[3,4-g]quinoline thus purified crystallized on evaporation of the ether; melting point=175°-7° C.; yield=40 mg.

Analysis: Calculated: C, 64.47; H, 9.02; N, 15.04; S, 11.47. Found: C, 64.47; H, 8.96; N, 15.09; S, 11.29.

The above purified free base tautomeric mixture was dissolved in ethanol and an excess of 12 N hydrochloric acid added. The volatile constituents were removed by evaporation and the resulting residue comprising the corresponding dihydrochloride salts crystallized from an acetone-methanol solvent mixture.

Analysis: Calculated: C, 51.13; H, 7.72; N, 11.93; Cl, 20.10; S, 9.10; Found: C, 50.89; H, 7.57; N, 12.15; Cl, 20.18; S, 9.31.

EXAMPLE 7

Preparation of trans-dl-5-methyl-4,4a,5,6,7,8,8a,9-octahydro-1H and 2H-pyrazolo[3,4-g]quinoline 46.5 g. of the isomer mixture containing about 60 percent of 6-benzoyloxy-3,4,5,6,7,8-hexahydro-1H-quinoline-2-one and 40% of the 3,4,4a,5,6,7-hexahydro isomer were dissolved in 400 ml. of tetrahydrofuran (THF). 80 ml. of methyl iodide were added and the resulting mixture cooled in an ice-water bath. 9.6 g of sodium hydride (as a 50 percent suspension in mineral oil) were added in portions. After all of the sodium hydride suspension had been added, the cooling bath was removed and the reaction mixture stirred at ambient temperature under a nitrogen atmosphere for about 4 hours. The reaction mixture was then diluted with water and the aqueous mixture thoroughly extracted with chloroform. The chloroform extracts were combined and the combined extracts washed with saturated aqueous sodium chloride and then dried. The chloroform was removed by evaporation to dryness in vacuo leaving as a residue an orange oil weighing 47.3 g. Crystallization of the residue from an ether-hexane solvent mixture yielded crystals of 1-methyl-6-benzoyloxy-3,4,5,6,7,8-hexahydro-2(1H)-quinolinone and the corresponding 3,4,4a,5,6,7-hexahydro isomer.

Analysis: Calculated: C, 71.56; H, 6.71; N, 4.91. Found: C, 71.33; H, 6.90; N, 4.67.

A solution of 47.3 g. of a mixture of 1-methyl-6-benzoyloxy-3,4,5,6,7,8-hexahydro-2(1H)-quinolinone and the corresponding 3,4,4a,5,6,7-hexahydro isomer as obtained above were dissolved in 800 ml. of THF and the solution cooled to about 0° C. 20 g. of lithium aluminumhydride were added thereto in portions and the resulting mixture refluxed for four hours under a nitrogen atmosphere. The reaction mixture was cooled and excess lithium aluminum-hydride destroyed by the addition of ethyl acetate. 10% sodium hydroxide was then added and the mixture diluted with water to decompose any organometallics present. The aqueous mixture was extracted several times with a chloroform-isopropanol solvent mixture. The organic extracts were combined and the combined extracts washed with saturated aqueous sodium chloride and then dried. Evaporation of the solvent yielded as a residue a mixture of the enamines—1-methyl-6-hydroxy-1,2,3,4,5,6,7,8-octahydroquinoline and 1-methyl-6-hydroxy-1,2,3,4,4a,5,6,7-octahydroquinoline—formed in the above reaction. (The lithium aluminumhydride reduction served to remove the benzoyl group at C-6 as a benzyl alcohol moiety, leaving a free hydroxyl in that position). The above residue, without further purification, was dissolved in about 300 ml. of ether and the ethereal solution saturated with gaseous hydrogen chloride, thus forming the hydrochloride salt of the enamine mixture. The ether was removed by decantation and the residue dissolved in a mixture of 200 ml. of THF and 50 ml. of methanol. This solution was cooled in an ice-water bath. 12 g. of sodium cyanoborohydride were added with cooling and stirring. After all of the cyanoborohydride had been added, the reaction mixture was stirred fo another 60 minutes and then poured over a mixture of ice and 1 N aqueous hydrochloric acid. The acidic aqueous solution was extracted with chloroform and the chloroform extract discarded. The solution was then made basic with 14 N aqueous ammonium hydroxide. Trans-dl-1-methyl-6-hydroxydecahydroquinoline formed in the above reaction, being insoluble in the alkaline medium, separated and was extracted several times with a chloroform-isopropanol solvent mixture. The combined extracts were washed with saturated aqueous sodium chloride and then dried. Evaporation of the solvent yielded 15 g. of trans-dl-1-methyl-6-hydroxydecahydroquinoline.

Fifteen grams of trans-dl-1-methyl-6-hydroxydecahydroquinoline were dissolved in 250 ml. of 6 N aqueous sulfuric acid. The solution was cooled in an ice-water bath. A solution of 9 g. of chromium trioxide in 60 ml. of 6 N aqueous sulfuric acid were added thereto with stirring in dropwise fashion over a 10-minute period. The cooling bath was removed and the reaction mixture stirred for an additional 60 minutes at ambient temperature. The excess oxidizing agent was decomposed by adding isopropanol to the reaction mixture. The reaction mixture was next poured over ice and the acidic aqueous solution made basic with 14 N aqueous ammonium hydroxide. trans-dl-1-Methyl-6-oxodecahydroquinoline thus formed, being insoluble in the alkaline layer, separated and was extracted several times with a mixture of chloroform and isopropanol. The extracts were combined and the combined extracts washed with saturated aqueous sodium chloride and then dried. Evaporation of the solvent in vacuo yielded trans-dl-1-methyl-6-oxodecahydroquinoline boiling in the range 105°–116° C. at 6 torr; yield=7.7 g. (45%).

A reaction mixture was prepared from 7.7 g. of trans-dl-1-methyl-6-oxodecahydroquinoline, 36 g. of the dimethyl acetal of dimethylformamide and 250 ml. of benzene. Benzene was removed by distillation at atmospheric pressure under nitrogen until about ½ the original volume remained (1.25 hours). Sufficient benzene was then added to make up the volume to the original volume and the process was repeated (four times). All of the benzene was finally removed by evaporation in vacuo and the resulting residue dissolved in 100 g. of dimethylformamide dimethylacetal. This solution was heated to refluxing temperature under nitrogen for 20 hours. The reaction mixture was then evaporated in vacuo and a chloroform solution of the residue chromatographed over 150 g. of florisil using as the eluant, methylene dichloride containing increasing amounts (1–5%) of methanol. Fractions containing similar substances as shown by TLC were combined. The third substance to be eluted was a yellow solid (wt=3 g. ) The solid was heated with 100 ml. of ether and the resulting solution filtered. Concentration of the filtrate to about 50 ml. yielded 590 mg. of crystals of trans-dl-1-methyl-6-oxo-7-dimethylaminomethylenedecahydroquinoline melting at 107°–109° C.

Analysis: Calculated: C, 70.23; H, 9.97; N, 12.60. Found: C, 70.17; H, 9.74; N, 12.87.

A solution was prepared by dissolving 175 mg. of trans-dl-1-methyl-6-oxo-7-dimethylaminomethylenedecahydroquinoline in 10 ml. of methanol. 0.05 ml. of hydrazine hydrate were added and the resulting reaction mixture stirred at room temperature under a nitrogen atmosphere for 4.5 days. The volatile constituents were removed by evaporation. A chloroform solution of the residue was chromatographed over 25 g. of florisil using chloroform containing increasing amounts (2–15%) of methanol as the eluant. Fractions shown by TLC to contain a substance moving close to the origin and different than starting material were combined and the solvent removed from the combined fractions by evaporation. trans-dl-5-methyl-4,4a,5,6,7,8,8a,9-octahydro-1H-(and 2H)-pyrazolo[3,4-g]quinoline free base gave a molecular ion (M+) at 191 by mass spectroscopy.

The resulting residue was dissolved in ethanol and 2 ml. of 1 N hydrochloric acid were added. The acidic solution was evaporated to dryness. Crystallization of the residue from ethanol yielded a tautomeric mixture containing trans-dl-5-methyl-4,4a,5,6,7,8,8a,9-octahydro-1H-(and 2H)-pyrazolo[3,4-g]quinoline dihydrochlorides melting at 268°–70° C. with decomposition; yield=140 mg.

Analysis: Calcualted: C, 50.01; H, 7.25; N, 15.90; Cl, 26.84. Found: C, 49.82; H, 7.08; N, 15.66; Cl, 26.80.

EXAMPLE 8

Alternate Preparation of
1-n-Propyl-6-benzoyloxy-3,4,5,6,7,8-hexahydro-2(1H)-quinolinone and
1-n-Propyl-6-benzolyloxy-3,4,4a,5,6,7-hexahydro-2(1H)-quinolinone A reaction mixture was prepared containing 4.4 g. of 4-benzoyloxycyclohexanone [prepared by the procedure of E. R. H. Jones and F. Sondheimer, *J. Chem. Soc.*, 615 (1949)], 2.5 ml. of n-propylamine and 100 ml. toluene. The mixture was heated to reflux temperature for about 2 hours under a nitrogen atmosphere using a Dean-Stark water trap. The reaction mixture was then heated to refluxing temperature for an additional 2 hours in the presence of a molecular sieve to remove water. The reaction mixture was cooled and the solvent removed by evaporation in vacuo. 4 ml. of methyl acrylate and 100 ml. of dioxane were added to the residue and the resulting mixture was refluxed overnight under a nitrogen atmosphere. The reaction mixture was again cooled and the volatile constituents removed by evaporation in vacuo. Chromatography of an ethereal solution of the resulting residue over 200 g. of florisil using ether as an eluant yielded a mixture of 1-n-propyl-6-benzoyloxy-3,4,5,6,7,8-hexahydro-2(1H)-quinolinone and 1-n-propyl-6-benzoyloxy-3,4,4a,5,6,7-hexahydro-2(1H)-quinolinone: yield=2.15 g.

EXAMPLE 9

Preparation of
trans-dl-5-allyl-4,4a,5,6,7,8,8a,9-octahydro-1H(and 2H)-pyrazolo[3,4-g]quinoline Following the procedure of Example 1, 65 g. of 4-benzoyloxycyclohexanone, 38 ml. of pyrrolidine and a few crystals of p-toluenesulfonic acid monohydrate were dissolved in 1000 ml. of cyclohexane. The resulting mixture was heated to reflux in a nitrogen atmosphere using a Dean-Stark water trap for about ½ hour. The mixture was then cooled and the solvents removed by evaporation in vacuo. The residue, comprising the pyrrolidine enamine of 4-benzoyloxycyclohexanone, was mixed with 53 g. of acrylamide in 1000 ml. of dioxane. The reaction mixture was heated to reflux temperature in a nitrogen atomsphere for about one day after which time it was cooled and the volatile constituents removed by evaporation. The resulting residue was diluted with water and the aqueous mixture extracted with ethyl acetate. The ethyl acetate extract was separated, washed with water and with saturated aqueous sodium chloride and then dried. Evaporation of the solvent yielded a mixture of 6-benzoyloxy-3,4,5,6,7,8-hexahydro-1H-quinoline-2-one and the corresponding 3,4,4a,5,6,7,-hexahydro compound.

The above mixture was dissolved in a combination of 250 ml. of tetrahyrofuran and 250 ml. of dimethylformamide. 12 g. of sodium hydride as a 50% suspension in mineral oil was added and the mixture stirred in order to completely form the sodium salt of the quinoline-2-one. Next 30 g. of allyl bromide as a solution in 75 ml. of THF were added and the resulting mixture stirred for 24 hours. The temperature of the reaction mixture rose rapidly and external cooling was supplied. After the reaction had been completed, the reaction mixture was diluted with water and the aqueous mixture extracted with ethyl acetate. The ethyl acetate extract was separated, washed with water and with saturated aqueous sodium chloride and then dried. Evaporation of the solvent yielded a mixture of 1-allyl-6-benzoyloxy-3,4,5,6,7,8-hexahydro-1H-quinoline-2-one and the corresponding 3,4,4a,5,6,7-hexahydro compound.

The N-allyl derivative thus prepared was dissolved in 750 ml. of THF and the solution cooled in an ice-water bath. 20 g. of lithium aluminum hydride were added thereto in portions. After the addition had been completed, the resulting mixture was heated to reflux temperature under a nitrogen atmosphere for about three hours. The reaction mixture was then cooled in an ice-water bath and the excess lithium aluminum hydride decomposed by the addition of ethyl acetate. 10% aqueous sodium hydroxide was added to decompose any organometallic compounds present and the mixture thus treated was diluted with water. The aqueous mixture was then extracted several times with chloroform and the chloroform extracts combined. The combined extracts were washed with saturated aqueous sodium chloride and dried. Evaporation of the solvent yielded a residue comprising a mixture of 1-allyl-6-hydroxy-1,2,3,4,5,6,7,8-octahydroquinoline and its 1,2,3,4,4a,5,6,7-octahydro isomer. The residue was dissolved in 750 ml. of ether and the ethereal solution saturated with anhydrous gaseous hydrogen chloride. The hydrochloride salt of the octahydroquinoline mixture, being insoluble in ether, precipitated and the ether was separated by decantation. The hydrochloride was dissolved in a mixture of 100 ml. of methanol and 300 ml. of THF. This solution was cooled in an ice-water bath. 20 g. of sodium cyanoborohydride were added thereto in portions while the reaction mixture was being cooled. After the addition had been completed, the cooling bath was removed. The reaction was stirred at ambient temperature for about 1 hour, and was then diluted with saturated aqueous sodium bicarbonate. The alkaline layer was extracted several times with chloroform. The chloroform extracts were combined and the combined extracts washed with saturated aqueous sodium chloride and then dried. Evaporation of the solvent yielded about 12.8 g. of trans-dl-1-allyl-6-hydroxydecahydroquinoline.

The trans-dl-1-allyl-6-hydroxy-decahydroquinoline thus prepared was dissolved in 500 ml. of methylenedichloride to which had been added 8.2 g. of sodium acetate. Next 21.6 g. of pyridine hydrochloride/chromium trioxide were added. The reaction was stirred for 7.5 hours under a nitrogen atmosphere at ambient temperature, and was then filtered. The filtrate was concentrated in vacuo. Chromatography of the filtrate over 10 g. of florisil using chloroform containing increasing amounts (1–5%) methanol as the eluant yielded 3.2 g. of trans-dl-1-allyl-6-oxodecahydroquinoline formed in the above reaction. The 6-oxo compound was dissolved in toluene and 25 ml. of dimethylformamide dimethylacetal were added. The reaction mixture was heated to reflux temperature under a nitrogen atmosphere for 24 hours after which time it was cooled and the solvent removed by evaporation. The resulting residue was chromatographed over 150 g. of florisil using chloroform containing increasing amounts (2–20%) of methanol as the eluant. Fractions shown by TLC to contain the desired trans-dl-1-allyl-6-oxo-7-dimethylaminomethylenedecahydroquinoline formed in the above reaction were combined to yield after evaporation of the solvent 1.3 g. of the desired product. This material was dissolved in 75 ml. of methanol to which was added 0.5 ml. of hydrazine hydrate. The reaction mixture was stirred at room temperature for about 20 hours after which time the volatile constituents were removed by evaporation in vacuo. A chloroform solution of the residue was chromatographed over 35 g. of florisil using chloroform containing increasing amounts (2-4%) of methanol as the eluant. Fractions shown by TLC to contain the desired trans-dl-5-allyl-4,4a,5,6,7,8,8a,9-octahydro-2H-pyrazolo[3,4-g]quinoline and its 1H tautomer were combined and the solvent removed therefrom by evaporation in vacuo. Mass spectroscopy of the residue gave a molecular ion at 217. The residue, weighing 0.55 g., was dissolved in 75 ml. of acetone and the acetone solution heated to reflux. 0.5 ml. of 12 N aqueous hydrochloric acid were added thereto in dropwise fashion. The reaction mixture was allowed to cool. Trans-dl-5-allyl-4,4a,5,6,7,8,8a,9-octahydro-2-H(and 1H)-pyrazolo[3,4-g]quinoline dihydrochloride thus prepared melted at about 215° C. with decomposition; weight=495 mg.

Analysis calculated: C, 53.80; H, 7.29; N, 1.48; Cl, 24.43 Found: C, 53.52; H, 7.13; N, 1.65; Cl, 24.17.

As evidence of the utility of the compounds of this invention, it has been found that they affect turning behavior in 6-hydroxydopamine-lesioned rats in a test procedure designed to uncover compounds useful for the treatment of Parkinsonism. In this test, nigroneostriatal-lesioned rats are employed, as prepared by the procedure of Ungerstedt and Arbuthnott, *Brain Res*, 24, 485 (1970). A compound having dopamine agonist activity causes the rats to turn in circles contralateral to the side of the lesion. After a latency period, which varies from compound to compound, the number of turns is counted over a 15-minute period.

Results obtained from testing representative compounds of this invention in the rat turning test are set forth in Table 1 below. The compounds were dissolved in water and the aqueous solution injected into the rat by the intraperitoneal route at dose levels of 1 mg/kg. and 100 mcg/kg. In the table, column 1 gives the name of the compound, column 2, percent of test animals exhibiting turning behavior, and column 3, average number of turns observed in first 15 minutes after end of latency period.

invention have been shown to inhibit prolactin according to the following procedure.

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the test drug. The purpose of the reserpine was to keep prolactin levels uniformly elevated. The compounds under test were dissolved in 10 percent ethanol, and were injected intraperitoneally at doses of 50 mcg/kg and 0.5 and 5 mg/kg. Each compound was administered at each dose level to a group of 10 rats, and a control group of 10 intact males received an equivalent amount of 10 percent ethanol. One hour after treatment, all rats were killed by decapitation, and 150 µl aliquots of serum were assayed for prolactin.

The difference between the prolactin level of the treated rats and prolactin level of the control rats, divided by the prolactin level of the control rats gives the percent inhibition of prolactin secretion attributable to the compounds of this invention. These inhibition percentages are given in Table 2 below. In the table, column 1 gives the name of the compound; and columns 2, 3 and 4, the percent prolactin inhibition at 50 mcg./kg, and 0.5 and 5 mg./kg. dose levels.

Table 2

| | Percent Prolactin Inhibition at Given Dose | | |
|---|---|---|---|
| Name of Compound | 50 mcg/kg | 0.5 mg/kg | 5 mg/kg |
| trans-dl-5-n-Propyl-4,4a,5,-6,7,8,8a,9-octahydro-1H (and 2H)-pyrazolo[3,4-g]quinoline dihydrochloride | 61 | — | 91 |
| trans-dl-5-Methyl-4,4a,5,6,-7,8,8a,9-octahydro-1H (and 2H)-pyrazolo[3,4-g]quinoline dihydrochloride | — | 42 | 84 |
| trans-dl-5-n-Propyl-7-methyl-mercaptomethyl-4,4a,5,6,7,8,8a,9-octahydro-1H (and 2H)-pyrazolo-[3,4-g]quinoline | — | 48 | 73 |

Table 1

| | % of Rats Exhibiting Turning Behavior | | Average Number of Turns/rat | |
|---|---|---|---|---|
| Name of Compound | 1 mg./kg. | 100 mcg./kg. | 1 mg./kg. | 100 mcg./kg. |
| trans-dl-5-n-Propyl-4,4a,-5,6,7,8,8a,9-octahydro-1H and 2H-pyrazolo[3,4-g]quinoline dihydrochloride | 100 | 75 | 80 | 66 |
| trans-dl-5-n-Propyl-7-methylmercaptomethyl-4,4a,5,6,7,8,8a,9-octahydro-1H and 2H-pyrazolo[3,4-g]-quinoline dihydrochloride | 100 | 50 | 81 | 67 |
| trans-dl-5-allyl-4,4a,5,6,-7,8,8a,9-octahydro-1H and 2H-pyrazolo[3,4-g]quinoline dihydrochloride | 100 | 0 | 165 | 0 |

The compounds of this invention are also useful as prolactin inhibitors and as such they can be employed in the treatment of inappropriate lactation such as postpartum lactation and galactorrhea. As evidence of their utility in the treatment of conditions in which it is desirable to reduce the prolactin level, the compounds of this In using the compounds of this invention to inhibit prolactin secretion or to treat Parkinson's syndrome or for other pharmacologic action, a compound according to Formula Ia or Ib above in which R is $C_1$-$C_3$ alkyl or allyl and $R^1$ is H or $CH_2X$ where X is $OCH_3$, $SCH_3$, $SO_2CH_3$, CN or $CONH_2$, or a salt thereof with a pharmaceutically-acceptable acid, is administered to a subject suffering from Parkinsonism or in need of having his or her prolactin level reduced in an amount effective to treat Parkinsonism or to reduce prolactin. Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a water soluble pharmaceutically-acceptable salt is employed. For oral administration, the compound either as the free base or in the form of a salt thereof, can also be mixed with standard pharmaceutical excipients and loaded into empty telescoping gelatin capsules or pressed into tablets. The oral dosage range is from about 0.01 to 10 mg./kg. of mammalian weight and the parenteral dose range from about 0.0025 to 2.5 mg./kg. Intraperitoneal dosages of 10–100 mg./kg. of trans-dl-5-n-propyl-4,4a,5,6,7,8,8a,9-octahydro-1H(and 2H)-pyrazolo[3,4-g]quinoline dihydrochloride resulted in no deaths, but dosages of 300 mg./kg. were fatal, indicating an $LD_{50}$ in the range 100–300 mg./kg.

We claim:

1. A mixture of trans-dl-Tautomers of the formula

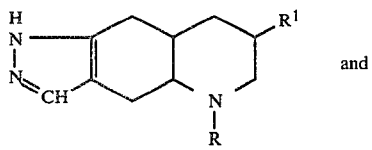
and
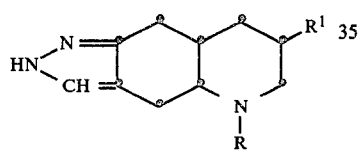

wherein R is H, CN, $C_1$–$C_3$ alkyl, allyl or benzyl and $R^1$ is H, COOH, COO($C_1$–$C_3$) alkyl or $CH_2X$ wherein X is CN, Cl, I, Br, OH, $OCH_3$, $SCH_3$, $SO_2CH_3$, $OSO_2$—($C_1$–$C_3$)—alkyl, O—$SO_2$—tolyl, $OSO_2$-phenyl or $CONH_2$ or a pharmaceutically-acceptable salt thereof.

2. A mixture of tautomers according to claim 1 in which R is $C_1$–$C_3$ alkyl or allyl and $R^1$ is H or $CH_2X$ wherein X is CN, $CONH_2$, $SCH_3$, $OCH_3$ or $SO_2CH_3$.

3. A mixture of tautomers according to claim 1 in which R is H, CN or benzyl and $R^1$ is H.

4. A mixture of tautomers according to claim 1 in which R is $C_1$–$C_3$ alkyl or allyl and $R^1$ is COO($C_1$–$C_3$) alkyl, or $CH_2X$ wherein X is Br, I, Cl, OH, $OSO_2$—($C_1$–$C_3$) alkyl, $OSO_2$-tolyl or $OSO_2$-phenyl.

5. A mixture of tautomers according to claim 1, said tautomers being trans-dl-5-n-propyl-4,4a,5,6,7,8,8a,9-octahydro-1H(and 2H)-pyrazolo[3,4-g]quinoline.

6. A mixture of tautomers according to claim 1, said tautomers being trans-dl-5-n-propyl-7-methylmercaptomethyl-4,4a,5,6,7,8,8a,9-octahydro-1H(and 2H)-pyrazolo[3,4-g]quinoline.

7. A mixture of the dihydrochloride salts of the tautomers of claim 5.

8. A mixture of the dihydrochloride salts of the tautomers of claim 6.

9. A mixture of tautomers according to claim 1, said tautomers being trans-dl-5-($C_1$–$C_3$)alkyl (or allyl)-7-($C_1$–$C_3$)alkoxy carbonyl-4,4a,5,6,7,8,8a,9-octahydro-1H(and 2H)-pyrazolo[3,4-g]quinoline.

10. A mixture of tautomers according to claim 9, said tautomers being trans-dl-5-n-propyl-7-ethoxycarbonyl-4,4a,5,6,7,8,8a,9-octahydro-1H(and 2H)-pyrazolo[3,4-g]quinoline.

11. A mixture of tautomers according to claim 9, said tautomers being trans-dl-5-methyl-7-ethoxycarbonyl-4,4a,5,6,7,8,8a,9-octahydro-1H(and 2H)-pyrazolo[3,4-g]quinoline.

12. A mixture of tautomers according to claim 1 in which R is $C_1$–$C_3$ alkyl or allyl, and $R^1$ is $CH_2X$ wherein X is CN, $CONH_2$, $SCH_3$, $SO_2CH_3$ and $OCH_3$.

13. A mixture of tautomers of claim 12 of the following formulae:

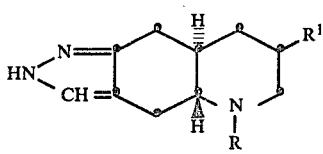
and
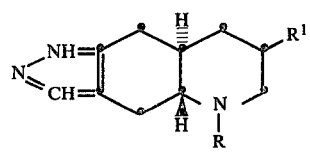

wherein R and $R^1$ have the same meaning as in claim 12.

14. A mixture of trans-dl compounds of the formula

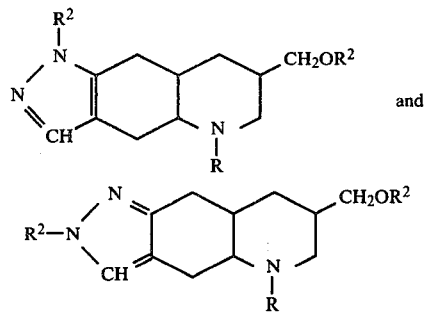

wherein R is $C_1$–$C_3$ alkyl or allyl and $R^2$ is $SO_2$($C_1$–$C_3$)alkyl, $SO_2$-tolyl or $SO_2CH_3$.

15. A pharmaceutical composition in unit dosage form adapted for administration to achieve a prolactin inhibiting effect, comprising per dosage unit, an amount of a compound according to claim 1 sufficient to inhibit the secretion of prolactin in combination with a pharmaceutically acceptable carrier or excipient.

16. A method of inhibiting the secretion of prolactin in mammals which consists of administering to a mammal having a condition in which there is an excess of prolactin being secreted, and in need of treatment, a dose of a compound according to claim 1 effective to reduce prolactin secretion.

* * * * *